(12) United States Patent
Imai

(10) Patent No.: US 9,752,991 B2
(45) Date of Patent: Sep. 5, 2017

(54) DEVICES, SYSTEMS, AND METHODS FOR ACQUISITION OF AN ANGULAR-DEPENDENT MATERIAL FEATURE

(71) Applicant: CANON KABUSHIKI KAISHA, Tokyo (JP)

(72) Inventor: Francisco Imai, Mountain View, CA (US)

(73) Assignee: Canon Kabushiki Kaisha, Tokyo (JP)

( * ) Notice: Subject to any disclaimer, the term of this patent is extended or adjusted under 35 U.S.C. 154(b) by 490 days.

(21) Appl. No.: 14/304,720

(22) Filed: Jun. 13, 2014

(65) Prior Publication Data

US 2015/0363927 A1 Dec. 17, 2015

(51) Int. Cl.
- *H04N 7/18* (2006.01)
- *G01N 21/88* (2006.01)
- *G01N 21/47* (2006.01)

(52) U.S. Cl.
CPC ..... *G01N 21/8806* (2013.01); *G01N 21/4738* (2013.01); *G01N 21/8851* (2013.01)

(58) Field of Classification Search
CPC ........ G06T 7/0008; G06T 2207/30124; H04N 7/188; H04N 7/181; G06K 7/10742; G01N 21/4738; G01N 21/8806; G01N 21/8851

See application file for complete search history.

(56) References Cited

U.S. PATENT DOCUMENTS

| | | | |
|---|---|---|---|
| 5,110,213 A * | 5/1992 | Seymour | G01N 21/86 131/908 |
| 6,987,568 B2 | 1/2006 | Dana | |
| 7,450,735 B1 | 11/2008 | Shah | |

(Continued)

FOREIGN PATENT DOCUMENTS

| | | |
|---|---|---|
| GB | 2478030 A | 8/2011 |
| JP | 2011003144 A | 1/2011 |

OTHER PUBLICATIONS

A. Del Bimbo et al., Pan-Tilt-Zoom Camera Networks, 2009.
Cha Zhang et al., Multi-View Imaging: Capturing and Rendering Interactive Environments, 2005.
Cha Zhang et al., A Self-Reconfigurable Camera Array, Eurographics Symposium on Rendering, 2004.

(Continued)

*Primary Examiner* — Sath V Perungavoor
*Assistant Examiner* — Xiaolan Xu
(74) *Attorney, Agent, or Firm* — Canon U.S.A., Inc. IP Division

(57) ABSTRACT

Systems, devices, and methods for detecting light obtain a first light-measurement objective, wherein a light-measurement objective defines one or more of an intensity of emitted light, a spectrum of emitted light, a spectrum of detected light, and a reflectance angle of detected light; obtain a second light-measurement objective; obtain an angular-dependence objective, wherein the angular-dependence objective defines a difference between a first light-reflection angle and a second light-reflection angle; select first settings values for one or more first illumination-emission devices and one or more first illumination-detection devices based on the first light-measurement objective; select second settings values for one or more second illumination-emission devices and one or more second illumination-detection devices based on the second light-measurement objective; and select a speed of an object conveyor based on the angular-dependence objective.

20 Claims, 9 Drawing Sheets

(56) References Cited

U.S. PATENT DOCUMENTS

| | | |
|---|---|---|
| 8,094,318 B2 | 1/2012 | Han |
| 8,253,792 B2 | 8/2012 | Wells |
| 8,345,252 B2 | 1/2013 | Nisper |
| 8,576,281 B2 | 11/2013 | Hammadou |
| 2003/0189703 A1* | 10/2003 | Yonezawa ............ G01N 21/956 356/237.2 |
| 2009/0213120 A1* | 8/2009 | Nisper .................... G01J 3/504 345/426 |
| 2010/0150404 A1 | 6/2010 | Marks |
| 2011/0273450 A1 | 11/2011 | Baril |
| 2012/0243730 A1 | 9/2012 | Outtagarts |
| 2013/0027546 A1 | 1/2013 | Hayashi |
| 2014/0147005 A1* | 5/2014 | Kavli .................... G07F 7/0609 382/103 |
| 2015/0144537 A1* | 5/2015 | Skaff ..................... G06N 7/005 209/577 |

OTHER PUBLICATIONS

Jinwei Gu et al., Discriminative Illumination: Per-Pixel Classification of Raw Materials based on Optimal Projections of Spectral BRDF, Jan. 2014.

The camera DOME, BTFDBB: BTF Database Bonn and Measurement Lab, University of Bonn, http://cg.cs.uni-bonn.de/en/projects/btfdbb/dome/, viewed on Jun. 10, 2014.

Paul Debevec, The Light Stages and Their Applications to Photoreal Digital Actors, 2012.

Paul Debevec et al., Acquiring the Reflectance Field of a Human Face, 2000.

The Light Stages at UC Berkeley and USC ICT, University of Southern California, downloaded from http://gl.ict.usc.edu/LightStages/ on Jun. 10, 2014.

Murakami Color Research Laboratory, GCMS-3 Goniospectrophotometer System, 2007.

Canon Inc., The Canon Story 2013/2014, 2013.

* cited by examiner

Light-Measurement Objectives 1
Object-Conveyor Speed: 4

| Angle | Light #1 | Light #2 | Camera #1 | Camera #2 |
|---|---|---|---|---|
| 120° | t = 3 | | | t = 3 |
| 110° | t = 5 | | t = 5 | |
| 100° | | t = 7 | t = 7 | |
| 90° | | t = 10 | | t = 10 |

Light-Measurement Objectives 2
Object-Conveyor Speed: 2

| Angle | Light #1 | Light #2 | Camera #1 | Camera #2 | Camera #3 |
|---|---|---|---|---|---|
| 135° | | t = 2; $\lambda$ = 9 µm | | t = 2 | |
| 122° | t = 5; $\lambda$ = 1µm | t = 5; $\lambda$ = 500 nm | t = 5 | | t = 5 |
| 107° | t = 11; $\lambda$ = 9 µm | | | t = 11 | |
| 100° | t = 13; $\lambda$ = 1 µm | | t = 13 | | |

FIG. 5

DEVICES, SYSTEMS, AND METHODS FOR ACQUISITION OF AN ANGULAR-DEPENDENT MATERIAL FEATURE

BACKGROUND

Technical Field

This description generally relates to the acquisition of material features.

Background

The angular and wavelength dependency of light incidence and reflection for a single ray of light on the surface of a material is described by the spectral bidirectional reflectance distribution function (BRDF). An extension of BRDF for modeling the appearance of non-uniform surfaces is given by the bidirectional texture function (BTF), which includes non-local scattering effects like inter-reflections, subsurface scattering, and shadowing.

SUMMARY

In one embodiment, system for inspecting materials comprises an object conveyor that has an adjustable speed; one or more illumination-emission devices; one or more illumination-detection devices; and one or more processing units that are configured to adjust the speed of the object conveyor and to synchronize the emission of illumination by the illumination-emission devices and the detection of illumination by the illumination-detection devices.

In one embodiment, method for measuring reflected light comprises obtaining a first light-measurement objective, wherein a light-measurement objective defines one or more of an intensity of emitted light, a spectrum of emitted light, a spectrum of detected light, and a reflectance angle of detected light; obtaining a second light-measurement objective; obtaining an angular-dependence objective, wherein the angular-dependence objective defines a difference between a first light-reflection angle and a second light-reflection angle; selecting first settings values for one or more first illumination-emission devices and one or more first illumination-detection devices based on the first light-measurement objective; selecting second settings values for one or more second illumination-emission devices and one or more second illumination-detection devices based on the second light-measurement objective; and selecting a speed of an object conveyor based on the angular-dependence objective.

In one embodiment a device for inspecting materials comprises a computer memory; and one or more processing units that are coupled to the computer memory, to an object conveyor that has an adjustable speed, to one or more illumination-emission devices, and to one or more illumination-detection devices, wherein the one or more processing units are configured to cause the device to obtain an angular-dependence objective, wherein the angular-dependence objective defines a difference between a first light-reflection angle and a second light-reflection angle; select a speed of the object conveyor based on the angular-dependence objective; configure one or more first illumination-emission devices and one or more first illumination-detection devices according to first settings values; activate the one or more first illumination-emission devices; activate the one or more first illumination-detection devices to generate first illumination readings; initiate motion of the object conveyor at the speed; configure one or more second illumination-emission devices and one or more second illumination-detection devices according to second settings values; activate the one or more second illumination-emission devices; and activate the one or more second illumination-detection devices to generate second illumination readings.

BRIEF DESCRIPTION OF THE DRAWINGS

FIG. 5 illustrates example embodiments of settings values for a system for the acquisition of an angular-dependent material feature.

DESCRIPTION

The following disclosure describes certain explanatory embodiments. Other embodiments may include alternatives, equivalents, and modifications. Additionally, the explanatory embodiments may include several novel features, and a particular feature may not be essential to some embodiments of the devices, systems, and methods that are described herein.

Figure 1:
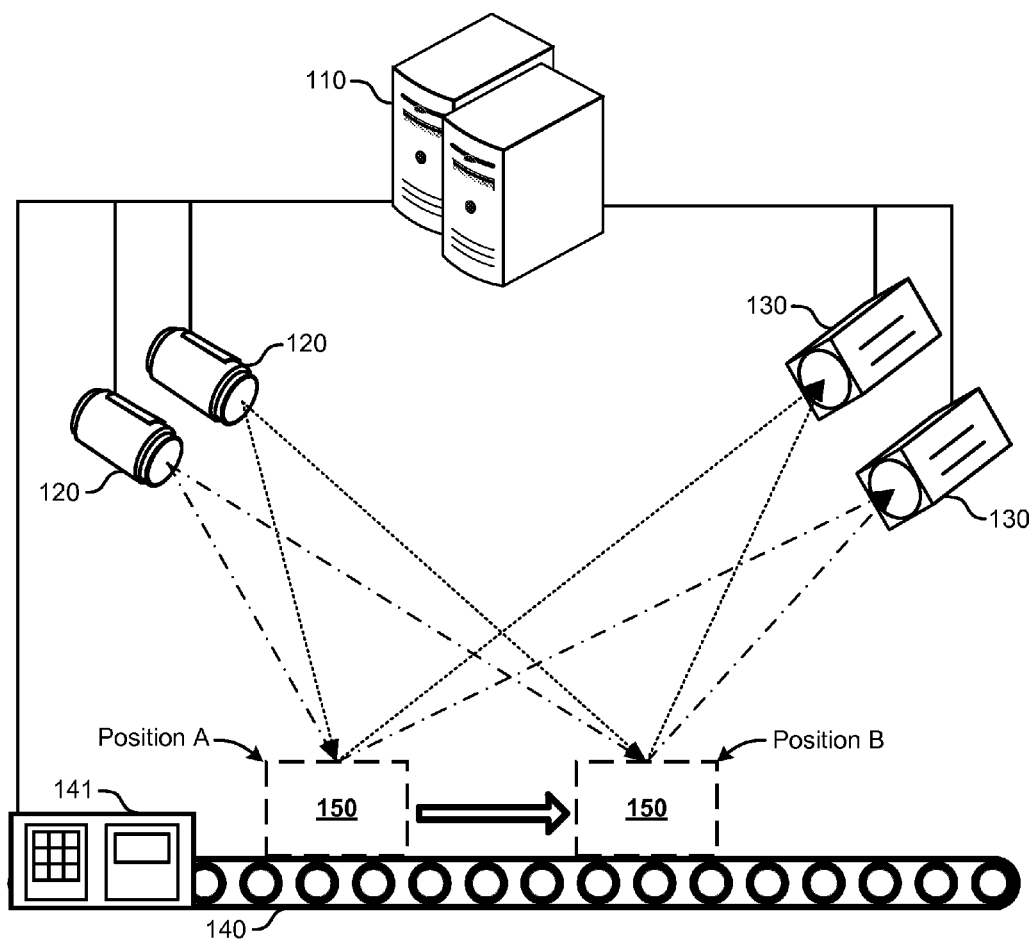
FIG. 1 illustrates an example embodiment of a system for the acquisition of an angular-dependent material feature.

FIG. 1 illustrates an example embodiment of a system for the acquisition of an angular-dependent material feature. The system includes one or more control devices 110, one or more illumination-emission devices 120, one or more illumination-detection devices 130, and an object conveyor 140. A control device 110 includes a computing device, for example, a desktop computer, a laptop computer, a tablet computer, a smartphone, a server, or a personal digital assistant. An illumination-emission device 120 emits lights and may be, for example, a laser or an LED. Also, an illumination-emission device 120 may be tunable (e.g., a tunable laser, a tunable LED) or may be used with a tunable filter, either of which allows an adjustment of the spectrum of light that is emitted by the illumination-emission device 120. Additionally, an illumination-emission device 120 may have other configurable settings, for example the polarization of emitted light, the filter (e.g., neutral density filters) that the device uses, the intensity of emitted light, and the orientation of the device (when the device is coupled to a movable mount and a motor).

An illumination-detection device 130 detects light and may be, for example, a camera (e.g., an RGB camera, a light-field camera) or a photometer. An illumination-detection device 130 may include a tunable sensor or a tunable filter, either of which allows an adjustment of the spectrum of light that is detected by the illumination-detection device 130. Also, an illumination-detection device 130 may have other configurable settings, for example dynamic range, shutter speed, aperture, signal gain (ISO), polarization, the filter used by the device, focal plane, and orientation (when the device is coupled to a movable mount and a motor).

The object conveyor 140 includes a control unit 141, which controls the operation of the object conveyor 140. The object conveyor 140 may be, for example, a belt conveyor, a roller conveyor, a bucket conveyor, a chain conveyor, and an electric-track vehicle system. In some embodiments, the conveyor surface remains stationary, but a mechanical arm or other device pushes objects across the conveyor surface. Additionally, in some embodiments one or more of the illumination-emission devices 120 or one or more of the illumination-detection devices 130 may be configured to move relative to the object 150 or the object conveyor 140, for example in embodiments where they are mounted on a movable arm, a gantry, a track, etc.

When the one or more illumination-detection devices 130 detect light that has been emitted by the one or more illumination-emission devices 120 and that has been reflected by an object 150, the one or more control devices 110 are configured to calculate the angle at which the light has been reflected by the object 150 based on the respective positions of the one or more illumination-emission devices 120, the respective positions of the one or more illumination-detection devices 130, and the position of the object 150. Thus, the system can capture light that has been reflected at different angles by the object 150 as the object moves. For example, when the object 150 is at position A, the system detects light that has been reflected at a different angle or at different angles then the reflected light that the system detects when the object 150 is at position B.

Figure 2:
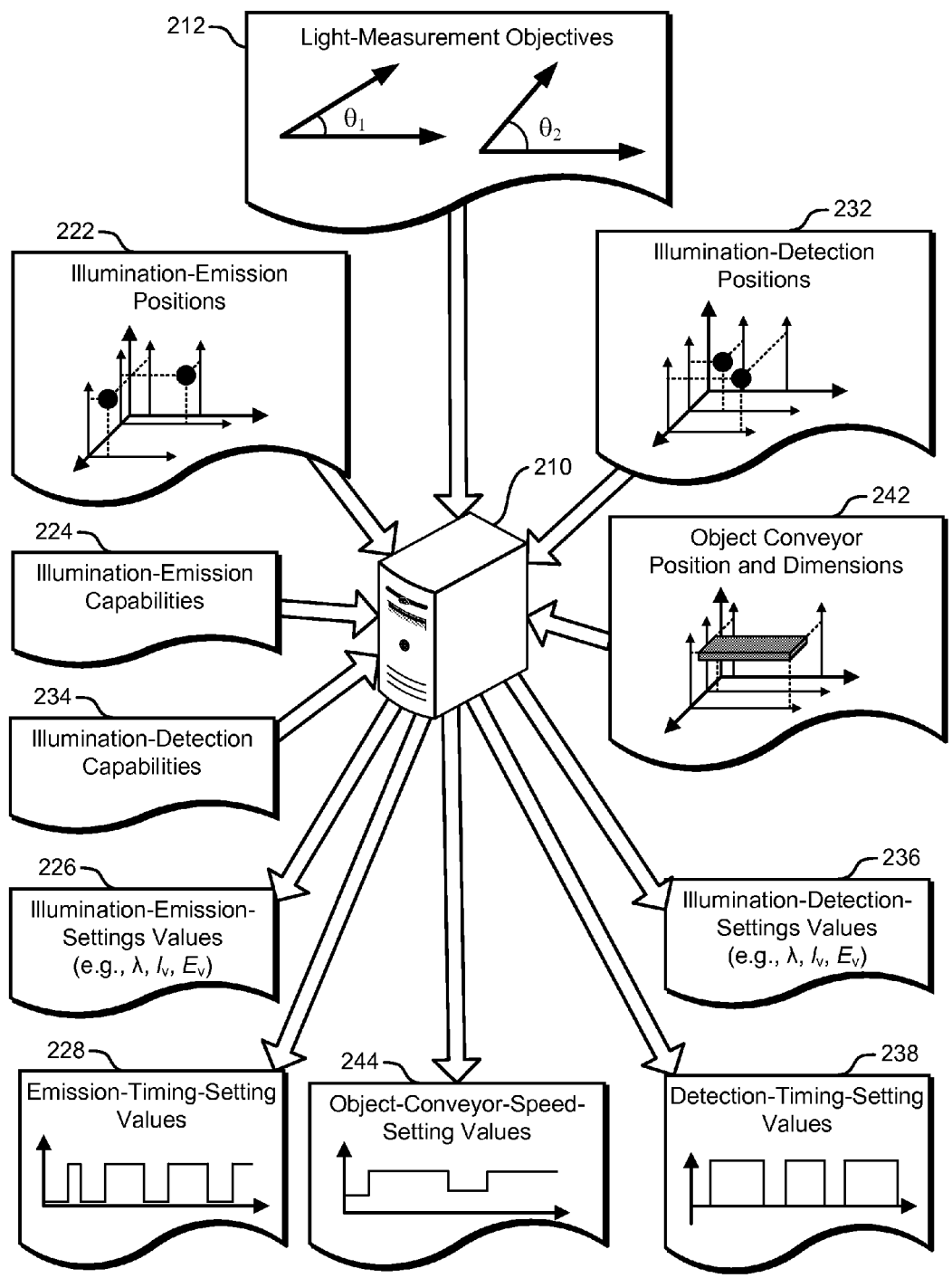
FIG. 2 illustrates an example embodiment of the inputs and outputs of a control device.

FIG. 2 illustrates an example embodiment of the inputs and outputs of a control device 210. The control device 210 obtains (e.g., by user input, by retrieving from memory, by requesting via a function call, by receiving from another device, by searching a data structure that is stored in a computer-readable medium) light-measurement objectives 212, illumination-emission positions 222, illumination-detection positions 232, illumination-emission capabilities 224, illumination-detection capabilities 234, and the position and dimensions of an object conveyor 242. The light-measurement objectives 212 define one or more properties of light for the system to measure. The properties of light may include a wavelength or spectrum of wavelengths of light, a polarization of light, and an angle of reflection of light, as well as other properties of light. The light-measurement objectives 212 may also include one or more angular-dependence objectives, which may include a light-reflection angle or a difference between a first light-reflection angle and a second light-reflection angle.

The illumination-emission positions 222 define the locations and orientations of respective illumination-emission devices. Also, the illumination-detection positions 232 define the locations and orientations of respective illumination-detection devices. And the position and dimensions of the object conveyor 242 define the location and dimensions of the object conveyor. For example, the illumination-emission positions 222, the illumination-detection positions 232, and the position and dimensions of the object conveyor 242 may be described in Cartesian coordinates or polar coordinates.

The illumination-emission capabilities 224 define the capabilities of respective illumination-emission devices. A setting's capabilities define the range of available values for the setting. The configurable settings of an illumination-emission device may include, for example, the spectrum of emitted illumination (e.g., for tunable devices), the intensity of emitted illumination, filters, strobe effects, and polarizers.

The illumination-detection capabilities 234 define the capabilities of respective illumination-detection devices. The configurable settings of an illumination-detection device may include, for example, the spectrum of detected light, gain, filters (e.g., polarizing filters), focus, and aperture.

Based on one or more of the light-measurement objectives 212, the illumination-emission positions 222, the illumination-detection positions 232, the illumination-emission capabilities 224, the illumination-detection capabilities 234, and the position and dimensions of the object conveyor 242, the control device 210 generates one or more of the following: illumination-emission-settings values 226, illumination-detection-settings values 236, emission-timing-setting values 228, detection-timing-setting values 238, and object-conveyor-speed-setting values 244.

The illumination-emission-settings values 226 define the values for one or more configurable settings of at least one illumination-emission device, and the illumination-detection-settings values 236 define the values for one or more configurable settings of at least one illumination-detection device. The emission-timing-setting values 228 define the time intervals during which one or more illumination-emission devices emit light. Also, these time intervals may indicate that the illumination-emission device should be continuously activated.

The detection-timing-setting values 238 define the time intervals during which one or more illumination-detection devices detect light. Additionally, these time intervals may indicate that the illumination-detection device should be continuously activated (e.g., capture a video).

Also, the object-conveyor-speed-setting values 244 define the speed at which the object conveyor moves objects. The emission-timing-setting values 228, the detection-timing-setting values 238, and the object-conveyor-speed-setting values 244 may be synchronized to allow the system to capture light that has been reflected by an object at the reflection angles that are defined in the light-measurement objectives 212.

Figure 3A:
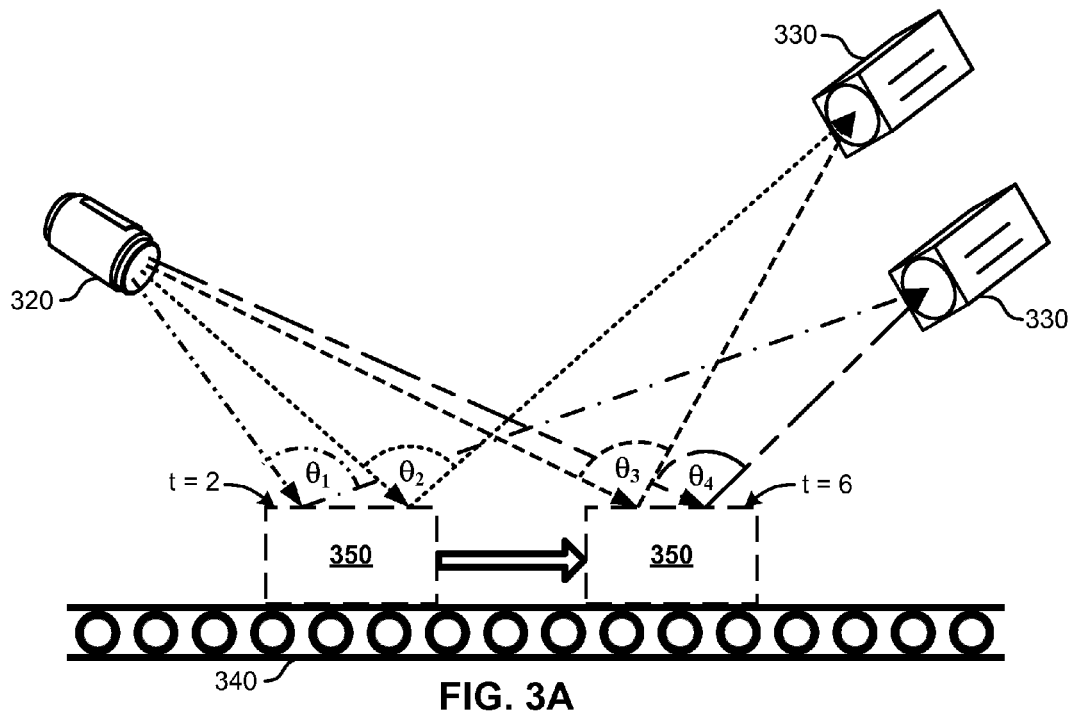
FIG. 3A and FIG. 3B illustrate examples of light-reflection angles of an object.
Figure 3B:
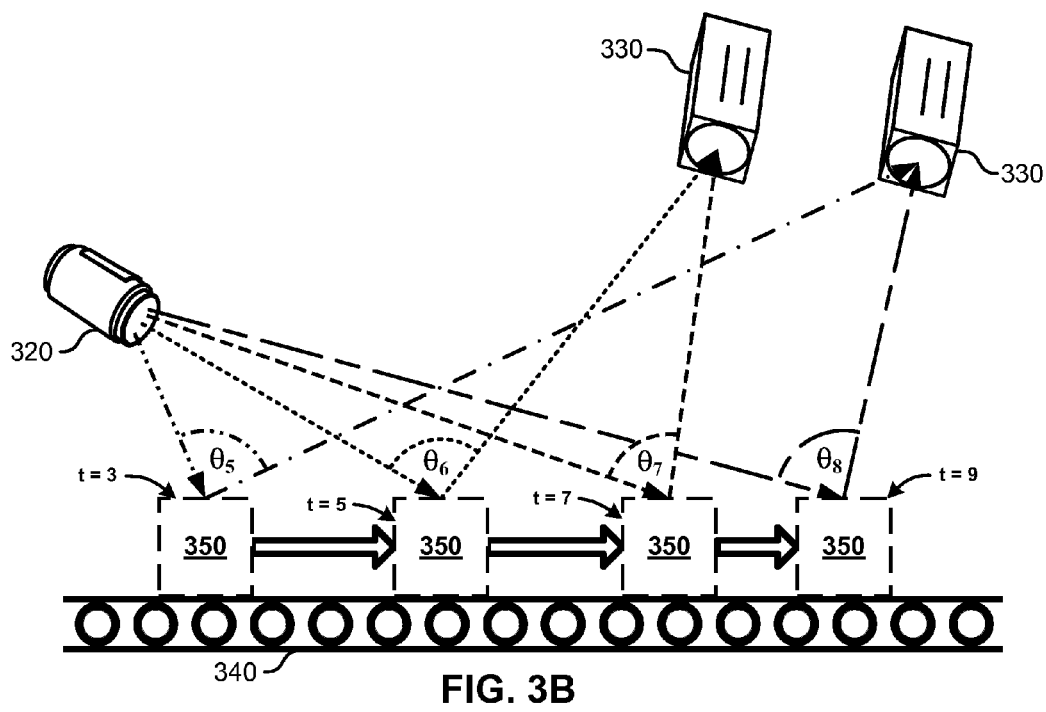

FIG. 3A and FIG. 3B illustrate examples of light-reflection angles of an object. FIG. 3A illustrates the light-reflection angles θ of the object 350 in a system that includes one illumination-emission device 320 and two illumination-detection devices 330. The light-reflection angles θ change as the object 350 is moved by the object conveyor 340. At time t=2, one of the illumination-detection devices 330 detects light that has been reflected at angle $\theta_1$, and another one of the illumination-detection devices 330 detects light that has been reflected at angle $\theta_2$. At time t=6, the object 350 has been moved to a new position, and one of the illumination-detection devices 330 detects light that has been reflected at angle $\theta_3$, and another one of the illumination-detection devices 330 detects light that has been reflected at angle $\theta_4$.

Thus, if received light-measurement objectives include detecting light that was reflected at angles $\theta_1$, $\theta_2$, $\theta_3$, and $\theta_4$, the system can generate emission-timing-setting values 228, detection-timing-setting values 238, and object-conveyor-speed-setting values 244 that configure the system to capture light that was reflected by the object 350 at angles $\theta_1$, $\theta_2$, $\theta_3$, and $\theta_4$.

FIG. 3B illustrates the light-reflection angles θ of an object 350 in a system that includes one illumination-emission device 320, two illumination-detection devices 330, and an object conveyor 340. In this example, the light-measurement objectives include four light-reflection angles: $\theta_5$, $\theta_6$, $\theta_7$, and $\theta_8$. The system generates emission-timing-setting values 228, detection-timing-setting values 238, and object-conveyor-speed-setting values 244 that configure the system to capture light that has been reflected by the object 350 at angles $\theta_5$, $\theta_6$, $\theta_7$, and $\theta_8$.

At time t=3, a first illumination-detection device 330 detects light that has been reflected at angle $\theta_5$. At time t=5, the object 350 has been moved to a new position, and a second illumination-detection device 330 detects light that has been reflected at angle $\theta_6$. At time t=7, the object 350 has been moved to another position, and the second illumination-detection device 330 detects light that has been reflected at angle $\theta_7$. Finally, at time t=9, the object 350 has been moved to a fourth position, and the first illumination-detection device 330 detects light that has been reflected at angle $\theta_8$.

Figure 4:
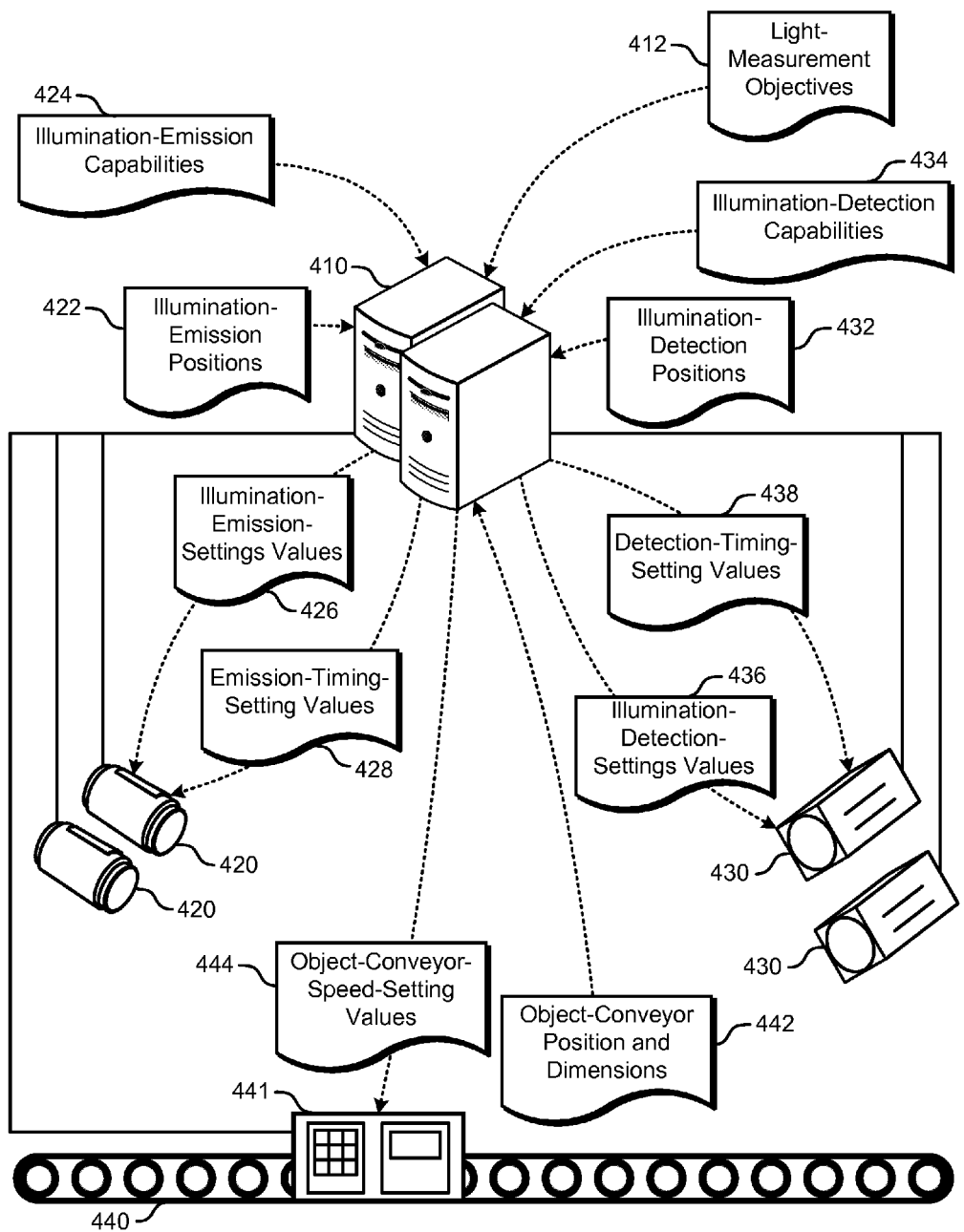
FIG. 4 illustrates an example embodiment of a system for the acquisition of an angular-dependent material feature.

FIG. 4 illustrates an example embodiment of a system for the acquisition of an angular-dependent material feature. The system includes two control devices 410, two illumination-emission devices 420, two illumination-detection devices 430, and an object conveyor 440 and its controller 441.

The control devices 410 obtain the following (e.g., from a user interface, from a database, from one or more other devices): light-measurement objectives 412, illumination-emission positions 422, illumination-emission capabilities 424, illumination-detection positions 432, illumination-detection capabilities 434, light-measurement objectives 412, and the object-conveyor position and dimensions 442.

Then, based on one or more of the light-measurement objectives 412, the illumination-emission positions 422, the illumination-emission capabilities 424, the illumination-detection positions 432, the illumination-detection capabilities 434, the light-measurement objectives 412, and the object-conveyor position and dimensions 442, the one or more control devices 410 generate illumination-emission-settings values 426, emission-timing-setting values 428, illumination-detection-settings values 436, detection-timing-setting values 438, and object-conveyor-speed settings 444. In some embodiments (e.g., embodiments in which the illumination-emission devices 420 and the illumination-detection devices 430 are controlled by one or more controllers that are independent of the control devices 410), the control devices 410 send the illumination-emission-settings values 426 and the emission-timing-setting values 428 to the illumination-emission devices 420; send the illumination-detection-settings values 436 and the detection-timing-setting values 438 to the illumination-detection devices 430; or send the object-conveyor-speed-setting values 444 to the controller 441 of the object conveyor 440.

In other embodiments (e.g., embodiments where the control devices 410 directly control the illumination-emission devices 420, the illumination-detection devices 430, and the object conveyor 440), the control devices 410 sends signals to the illumination-emission devices 420, the illumination-detection devices 430, and the object conveyor 440 to control their operations according to the illumination-emission-settings values 426, the emission-timing-setting values 428, the illumination-detection-settings values 436, the detection-timing-setting values 438, and the object-conveyor-speed-settings values 444. For example, the one or more control devices 410 may send a capture signal to an illumination-detection device 430 at each predetermined moment that the illumination-detection device 430 should capture an image.

FIG. 5 illustrates example embodiments of settings values for a system for the acquisition of an angular-dependent material feature. A first group of settings values, which are for light-measurement objectives 1, define the settings values for the system when the light-measurement objectives include capturing light that has been reflected at the following angles: 120°, 110°, 100°, and 90°. The settings values indicate that the speed of the object conveyor is 4. The settings values also indicate that a first illumination-emission device, light #1, should be activated at t=3 and t=5; that a second illumination-emission device, light #2, should be activated at t=7 and t=10; that a first illumination-detection device, camera #1, should be activated at t=5 and t=7; and that a second illumination-detection device, camera #2, should be activated at t=3 and t=10.

Also, a second group of settings values, which are for light-measurement objectives 2, define the settings values for the system when the light-measurement objectives include capturing light that has been reflected at the following angles: 135°, 122°, 107°, and 100°. The settings values indicate that the speed of the object conveyor is 2. In this embodiment, in addition to the timing, the settings values also indicate the wavelength of the illumination-emission devices. The settings values indicate that a first illumination-emission device, light #1, should be activated at t=5 to output light at $\lambda$=1 µm, at t=11 to output light at $\lambda$=9 µm, and t=13 to output light at $\lambda$=1 µm; that a second illumination-emission device, light #2, should be activated at t=2 to output light at $\lambda$=9 µm and at t=5 to output light at $\lambda$=500 nm; that a first illumination-detection device, camera #1, should be activated at t=5 and t=13; that a second illumination-detection device, camera #2, should be activated at t=2 and t=11; and that a third illumination-detection device, camera #3, should be activated at t=5. In alternative to or in addition to the wavelength of the illumination-emission devices, some embodiments include values for other settings of the devices, for example values for the dynamic range, shutter speed, aperture, signal gain (ISO), polarization, and focal plane of an illumination-detection device.

Figure 6:
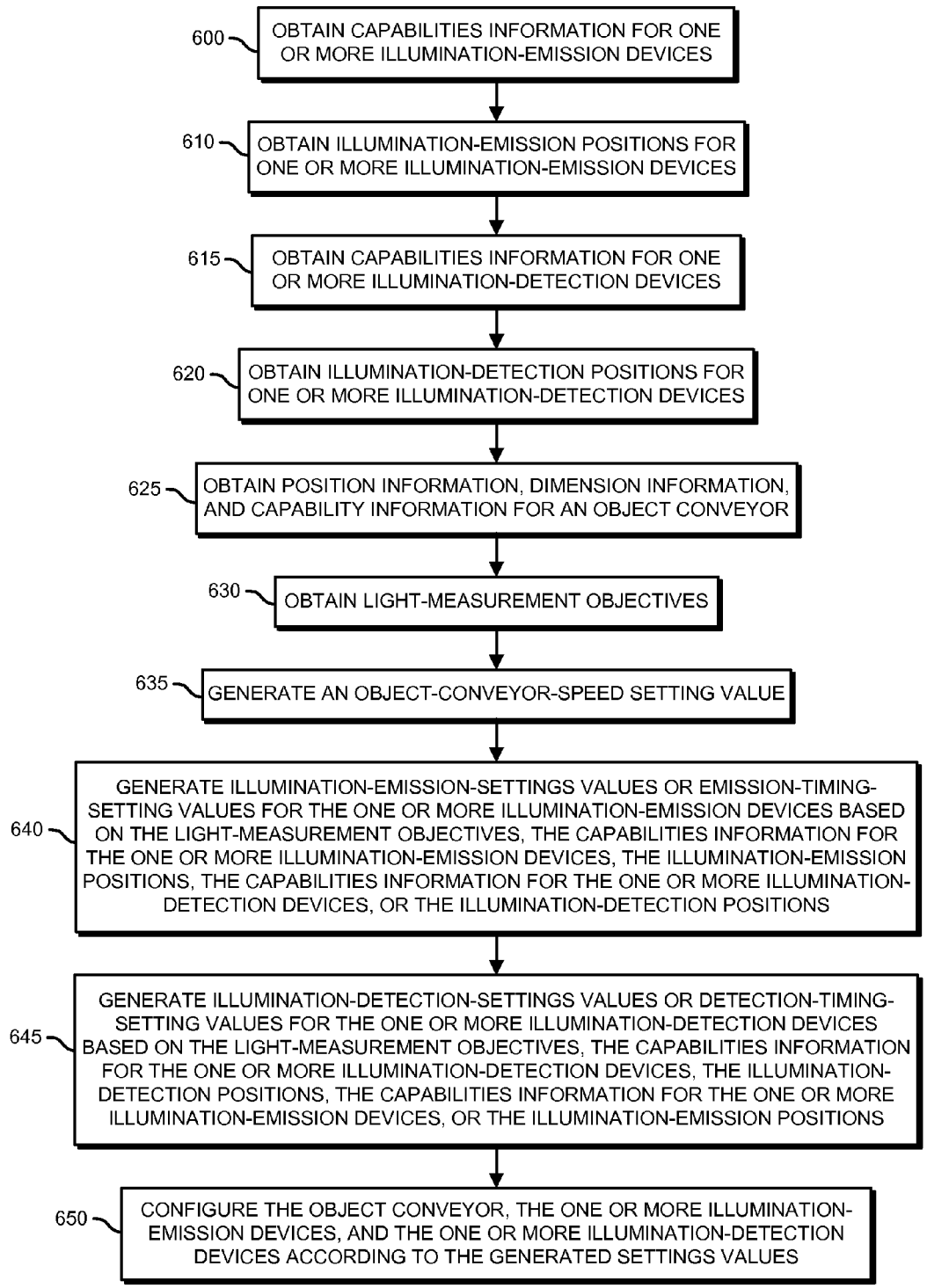
FIG. 6 illustrates an example embodiment of an operational flow for the acquisition of an angular-dependent material feature.

FIG. 6 illustrates an example embodiment of an operational flow for the acquisition of an angular-dependent material feature. The blocks of this operational flow and the other operational flows that are described herein may be performed by one or more computing devices, for example the computing devices described herein. Also, although this operational flow and the other operational flows that are described herein are each presented in a certain order, some embodiments may perform at least some of the operations in different orders than the presented orders. Examples of possible different orderings include concurrent, overlapping, reordered, simultaneous, incremental, and interleaved orderings. Thus, other embodiments of this operational flow and the other operational flows that are described herein may omit blocks, add blocks, change the order of the blocks, combine blocks, or divide blocks into more blocks.

The flow starts in block 600, where capabilities information for one or more illumination-emission devices is obtained (e.g., from user entry, from a storage device, from information that was transmitted by means of a network). Next, in block 610, information that describes the respective illumination-emission positions of the one or more illumination-emission devices is obtained. The flow then moves to block 615, where capabilities information for one or more illumination-detection devices is obtained. The flow then proceeds to block 620, where information that describes the respective illumination-detection positions of the one or more illumination-detection devices is obtained. Then in block 625, position information, dimension information, and capability information for an object conveyor are obtained.

The flow moves to block 630, where light-measurement objectives are obtained. Next, in block 635, an objectconveyor-speed-setting value is generated based on one or more of the light-measurement objectives, the position information for the object conveyor, the dimension information for the object conveyor, and the capability information for the object conveyor. In some embodiments, the object-conveyor-speed-setting value is further based on one or more of the capabilities information for the one or more illumination-emission devices, the capabilities information for the one or more illumination-detection devices, the illumination-emission positions of the one or more illumination-emission devices, and the illumination-detection positions of the one or more illumination-detection devices.

The flow moves to block 640, where illumination-emission-settings values or emission-timing-setting values are generated for the one or more illumination-emission devices based on the light-measurement objectives, the capabilities information for the one or more illumination-emission devices, the capabilities information for the one or more illumination-detection devices, the illumination-emission positions of the one or more illumination-emission devices, and the illumination-detection positions of the one or more illumination-detection devices.

Next, in block 645, illumination-detection-settings values or detection-timing-setting values are generated for the one or more illumination-emission devices based on the light-measurement objectives, the capabilities information for the one or more illumination-emission devices, the capabilities information for the one or more illumination-detection devices, the illumination-emission positions of the one or more illumination-emission devices, and the illumination-detection positions of the one or more illumination-detection devices.

Finally, in block 650, the object conveyor, the one or more illumination-emission devices, and the one or more illumination-detection devices are configured according to the generated settings values.

Figure 7:
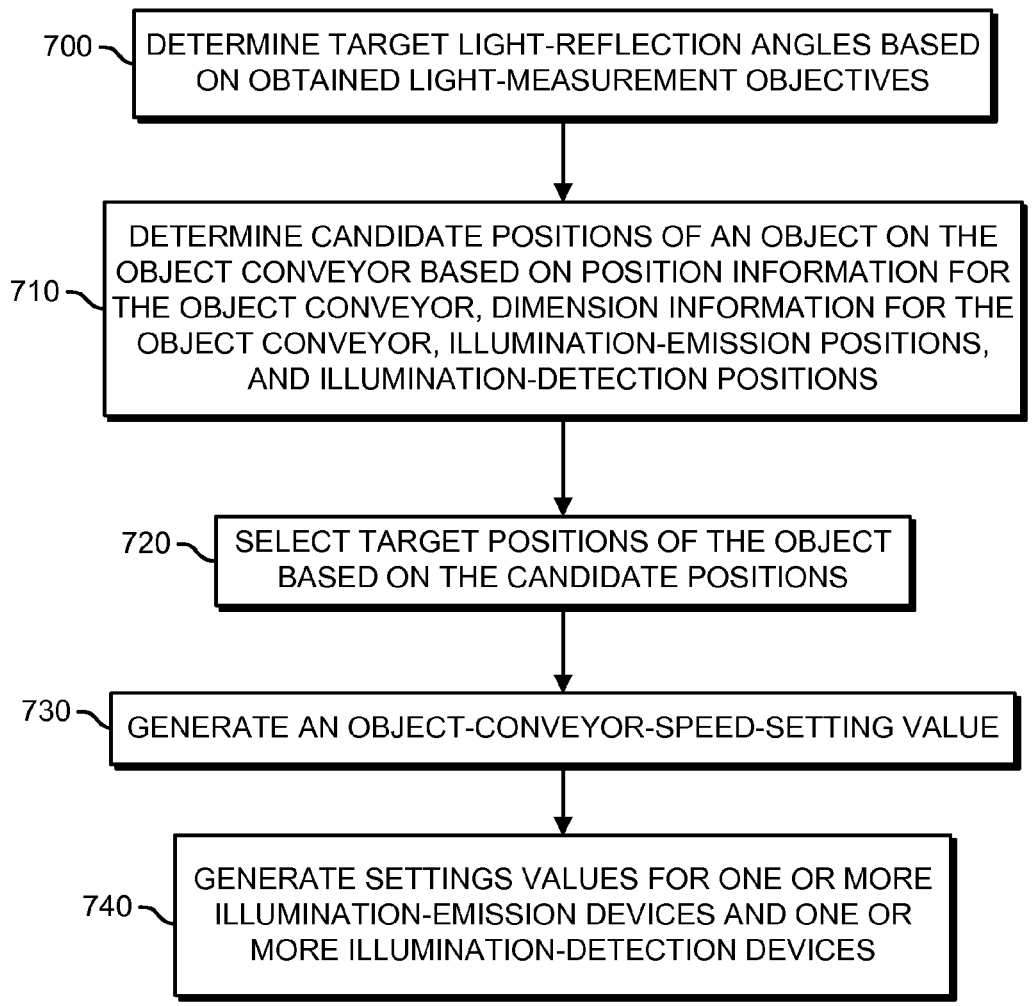
FIG. 7 illustrates an example embodiment of an operational flow for the acquisition of an angular-dependent material feature.

FIG. 7 illustrates an example embodiment of an operational flow for the acquisition of an angular-dependent material feature. The flow starts in block 700, where target light-reflection angles are determined based on obtained light-measurement objectives. Next, in block 710, candidate positions, which are positions of an object on the object conveyor where the system can detect light that has been reflected by the object at the target light-reflection angles, are determined based on at least some of the following: position information for an object conveyor, dimension information for the object conveyor, illumination-emission positions of one or more illumination-emission devices, and illumination-detection positions of one or more illumination-detection devices. In some embodiments and in some circumstances, the system can detect light that has been reflected by the object at the target light-reflection angle in multiple positions of the object on the object conveyor. For example, if the target light-reflection angle is 90°, there may be a first candidate position where a first illumination-detection device can detect light that was emitted by a first illumination-emission device and that was reflected at 90° by an object, and there may be a second candidate position where a second illumination-detection device can detect light that was emitted by a second illumination-emission device and that was reflected at 90° by the object.

The flow then proceeds to block 720, where target positions of the object are selected based on the candidate positions. For example, if two light-reflection angles are to be captured; if a first target angle can be detected at a first position, a second position, and a third position; and if a second target angle can be detected only at the first position, then, in some embodiments, the first and second position may be selected or the first and third position may be selected.

Next, in block 730, an object-conveyor-speed-setting value is generated based on one or more of the following: the target positions, the illumination-emission capabilities, and the illumination-detection capabilities. Finally, in block 740, settings values are generated for the one or more illumination-emission devices, the one or more illumination-detection devices, or both. The settings values include settings values for one or more of the following: illumination-emission settings, emission-timing settings, illumination-detection settings, and detection-timing settings.

Figure 8:
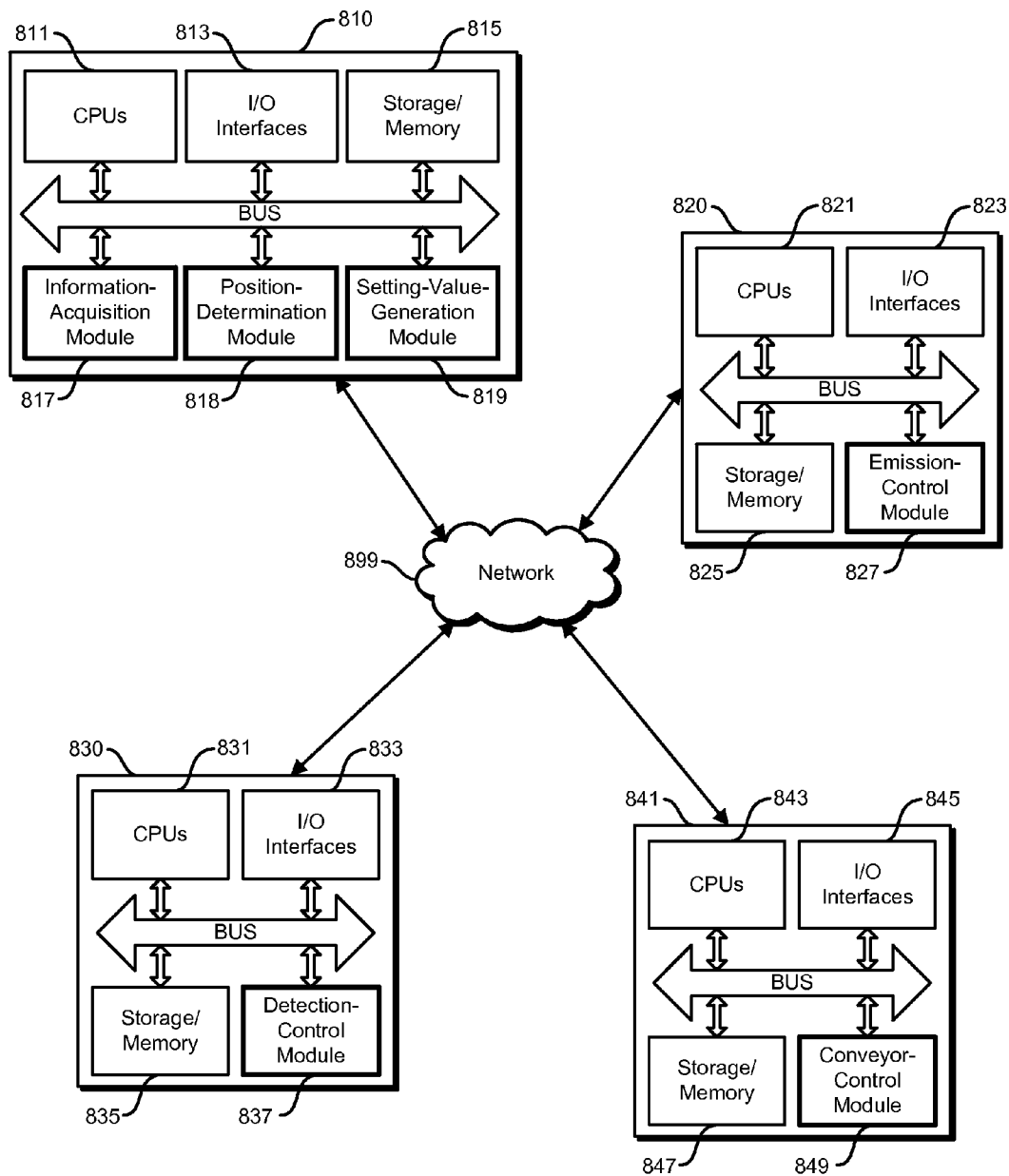
FIG. 8 illustrates an example embodiment of a system for the acquisition of an angular-dependent material feature.

FIG. 8 illustrates an example embodiment of a system for the acquisition of an angular-dependent material feature. The system includes a control device 810, an illumination-emission device 820, an illumination-detection device 830, and an object-conveyor controller 841. In this embodiment, the devices communicate by means of one or more networks 899, which may include a wired network, a wireless network, a LAN, a WAN, a MAN, and PAN, etc.

The control device 810 includes one or more processors (CPUs) 811, I/O interfaces 813, and storage/memory 815. The CPUs 811 includes one or more central processing units, which include microprocessors (e.g., a single core microprocessor, a multi-core microprocessor) or other circuits, and the CPU 811 is configured to read and perform computer-executable instructions, such as instructions in storage, in memory, or in a module. The I/O interfaces 813 include communication interfaces to input and output devices, which may include a keyboard, a display, a mouse, a printing device, a touch screen, a light pen, an optical-storage device, a scanner, a microphone, a camera, a drive, and a network (either wired or wireless).

The storage/memory 815 includes one or more computer-readable or computer-writable media, for example a computer-readable storage medium. A computer-readable storage medium, in contrast to a mere transitory, propagating signal, includes a tangible article of manufacture, for example a magnetic disk (e.g., a floppy disk, a hard disk), an optical disc (e.g., a CD, a DVD, a Blu-ray), a magneto-optical disk, magnetic tape, and semiconductor memory (e.g., a non-volatile memory card, flash memory, a solid-state drive, SRAM, DRAM, EPROM, EEPROM). The storage/memory 815 can store computer-readable data or computer-executable instructions. The components of the control device 810 communicate via a bus.

The control device 810 also includes an information-acquisition module 817, a position-determination module 818, and a setting-value-generation module 819. A module includes logic, computer-readable data, or computer-executable instructions, and may be implemented in software (e.g., Assembly, C, C++, C#, Java, BASIC, Perl, Visual Basic), hardware (e.g., customized circuitry), or a combination of software and hardware. In some embodiments, the devices in the system include additional or fewer modules, the modules are combined into fewer modules, or the modules are divided into more modules.

The information-acquisition module 817 includes instructions that, when executed, or circuits that, when activated, cause the control device 810 to obtain one or more of the following: light-measurement objectives, illumination-emission positions, illumination-emission capabilities, illumination-detection positions, illumination-detection capabilities, and the position and dimensions of an object conveyor. The obtaining may include generating a user interface that is configured to accept user entry of at least some of the information, sending a query to another device (e.g., the illumination-emission device 820, the illumination-detection device 830, the object-conveyor controller 841), or searching the storage/memory 815.

The position-determination module 818 includes instructions that, when executed, or circuits that, when activated, cause the control device 810 to determine target positions and, in some embodiments, candidate positions of an object based on light-measurement objectives, illumination-emission positions, illumination-detection positions, and the position and dimensions of an object conveyor.

The setting-value-generation module 819 includes instructions that, when executed, or circuits that, when activated, cause the control device 810 to generate settings values for one or more of the following: illumination-emission settings, emission-timing settings, illumination-detection settings, detection-timing settings, and object-conveyor-speed settings.

The illumination-emission device 820 includes one or more processors (CPUs) 821, I/O interfaces 823, storage/memory 825, an emission-control module 827, and at least one illumination-emission component (e.g., a laser, an LED light) that emits illumination. The emission-control module 827 includes instructions that, when executed, or circuits that, when activated, cause the illumination-emission device 820 to configure the illumination-emission component according to received illumination-emission-settings values and to activate and deactivate the illumination-emission component, for example according to received emission-timing-setting values.

The illumination-detection device 830 includes one or more processors (CPUs) 831, I/O interfaces 833, storage/memory 835, a detection-control module 837, and at least one illumination-detection component (e.g., a CMOS sensor, a CCD sensor) that detects illumination. The detection-control module 837 includes instructions that, when executed, or circuits that, when activated, cause the illumination-detection device 830 to configure the illumination-detection component according to received illumination-detection-settings values and to activate and deactivate the illumination-detection component, for example according to received detection-timing-setting values.

The object-conveyor controller 841 includes one or more processors (CPUs) 843, I/O interfaces 845, storage/memory 847, and a conveyor-control module 849, and is coupled to and controls an object conveyor. The conveyor-control module 849 includes instructions that, when executed, or circuits that, when activated, cause the object-conveyor controller 841 to activate or deactivate the object conveyor, for example according to received object-conveyor-speed-setting values.

Figure 9:
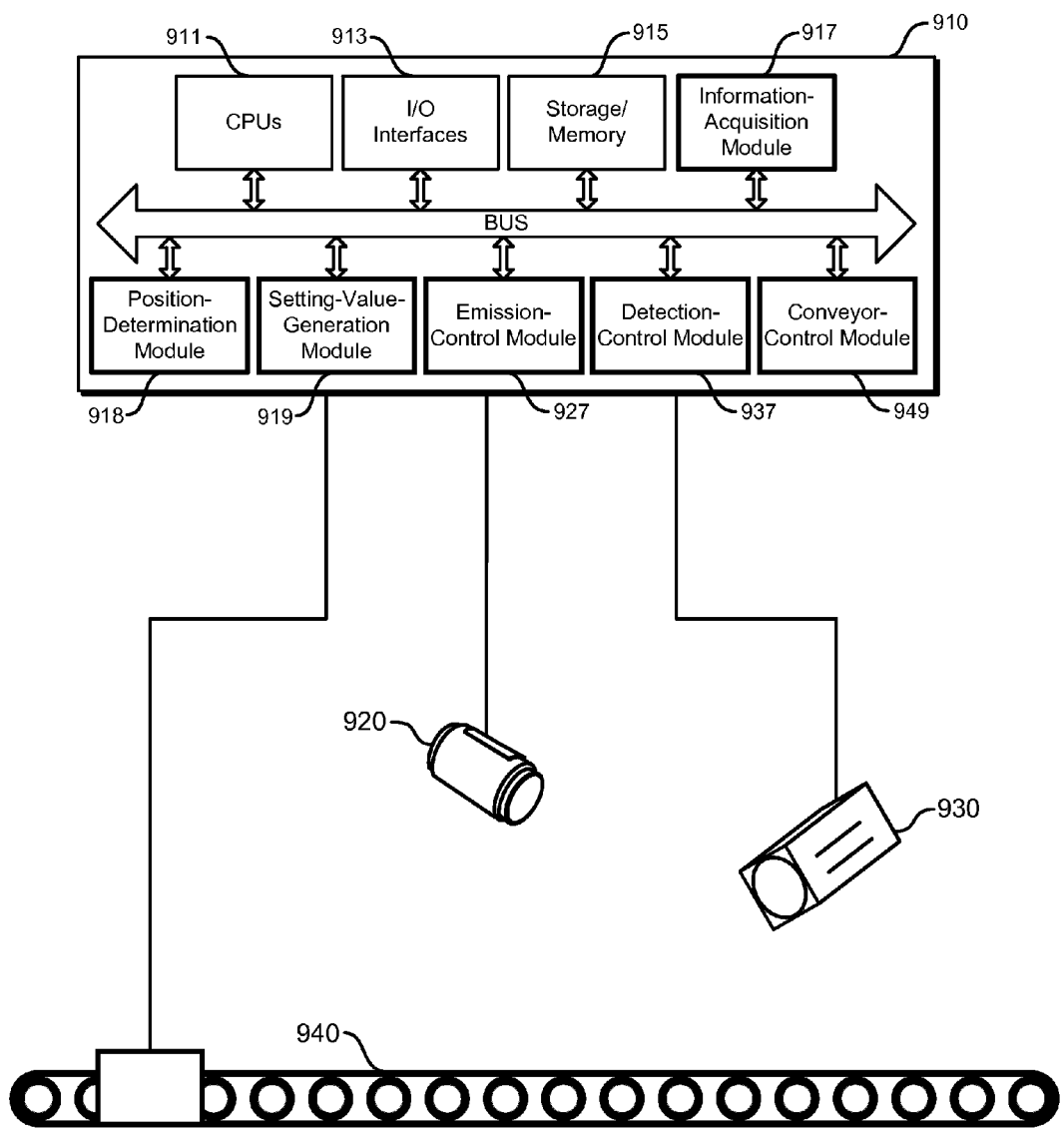
FIG. 9 illustrates an example embodiment of a system for the acquisition of an angular-dependent material feature.

FIG. 9 illustrates an example embodiment of a system for the acquisition of an angular-dependent material feature. The system includes a control device 910, an illumination-emission device 920, an illumination-detection device 930, and an object conveyor 940. The control device includes an information-acquisition module 917, a position-determination module 918, a setting-value-generation module 919, an emission-control module 927, a detection-control module 937, and a conveyor-control module 949. In this embodiment, the control device 910 controls the operations of the illumination-emission device 920, the illumination-detection device 930, and the object conveyor 940.

The above-described devices and systems can be implemented, at least in part, by providing one or more computer-readable media that contain computer-executable instructions for realizing the above-described operations to one or more computing devices that are configured to read and execute the computer-executable instructions. The systems or devices perform the operations of the above-described embodiments when executing the computer-executable instructions. Also, an operating system on the one or more systems or devices may implement at least some of the operations of the above-described embodiments.

Any applicable computer-readable medium (e.g., a magnetic disk (including a floppy disk, a hard disk), an optical disc (including a CD, a DVD, a Blu-ray disc), a magneto-optical disk, a magnetic tape, and semiconductor memory (including flash memory, DRAM, SRAM, a solid state drive, EPROM, EEPROM)) can be employed as a computer-readable medium for the computer-executable instructions. The computer-executable instructions may be stored on a computer-readable storage medium that is provided on a function-extension board inserted into a device or on a function-extension unit connected to the device, and a CPU provided on the function-extension board or unit may implement at least some of the operations of the above-described embodiments.

The scope of the claims is not limited to the above-described embodiments and includes various modifications and equivalent arrangements. Also, as used herein, the conjunction "or" generally refers to an inclusive "or," though "or" may refer to an exclusive "or" if expressly indicated or if the context indicates that the "or" must be an exclusive "or."

What is claimed is:

1. A system for inspecting materials, the system comprising:
    an object conveyor that has an adjustable speed;
    one or more illumination-emission devices;
    one or more illumination-detection devices; and
    one or more processing units that are configured to cause the system to
        control the speed of the object conveyor, the emission of illumination by the illumination-emission devices, and the detection of illumination by the illumination-detection devices,
        receive light-measurement objectives, and
        configure the speed of the object conveyor, the emission of illumination by the illumination-emission devices, and the detection of illumination by the illumination-detection devices based on the light-measurement objectives.

2. The system of claim 1, wherein the one or more processing units are further configured to cause the system to adjust one or more illumination-emission settings of the one or more illumination-emission devices and to adjust one or more illumination-detection settings of the one or more illumination-detection devices.

3. The system of claim 1, wherein the illumination-detection devices include one or more of the following: a vector of cameras, an array of cameras, and a line sensor.

4. The system of claim 1, wherein the illumination-emission devices include one or more of the following: an LED and a laser.

5. The system of claim 1, wherein the light-measurement objectives include identifying an angular dependency of light that is reflected by a target object that is positioned on the object conveyor.

6. The system of claim 1, wherein, to configure the speed of the object conveyor, the emission of illumination by the illumination-emission devices, and the detection of illumination by the illumination-detection devices based on the light-measurement objectives, the one or more processing units are further configured to cause the system to
- determine target light-reflection angles based on the light-measurement objectives;
- select target positions of an object on the object conveyor based on the target light-reflection angles; and
- calculate the speed of the object conveyor based on the target positions.

7. The system of claim 6, wherein, to configure the speed of the object conveyor, the emission of illumination by the illumination-emission devices, and the detection of illumination by the illumination-detection devices based on the light-measurement objectives, the one or more processing units are further configured to cause the system to
- generate one or more settings values for the illumination-emission devices and one or more settings values for the illumination-detection devices based on the target positions.

8. The system of claim 7, wherein the one or more settings values for the illumination-emission devices are illumination-emission-settings values and the one or more settings values for the illumination-detection devices are illumination-detection-settings values.

9. The system of claim 7, wherein the one or more settings values for the illumination-emission devices are illumination-timing-settings values and the one or more settings values for the illumination-detection devices are illumination-timing-settings values.

10. A method for measuring reflected light, the method comprising:
- obtaining a first light-measurement objective, wherein a light-measurement objective defines one or more of an intensity of emitted light, a spectrum of emitted light, a spectrum of detected light, and a reflectance angle of detected light;
- obtaining a second light-measurement objective;
- obtaining an angular-dependence objective, wherein the angular-dependence objective defines a difference between a first light-reflection angle and a second light-reflection angle;
- selecting first settings values for one or more first illumination-emission devices and one or more first illumination-detection devices based on the first light-measurement objective;
- selecting second settings values for one or more second illumination-emission devices and one or more second illumination-detection devices based on the second light-measurement objective; and
- selecting a speed of an object conveyor based on the angular-dependence objective.

11. The method of claim 10, further comprising:
- configuring the one or more first illumination-emission devices and the one or more first illumination-detection devices according to the first settings values;
- activating movement of the object conveyor according to the speed;
- activating the one or more first illumination-emission devices;
- activating the one or more first illumination-detection devices to generate first illumination readings;
- configuring the one or more second illumination-emission devices and the one or more second illumination-detection devices according to the second settings values;
- activating the one or more second illumination-emission devices; and
- activating the one or more second illumination-detection devices to generate second illumination readings.

12. The method of claim 11, further comprising:
- determining an angular dependency of reflected light based on the first illumination readings and the second illumination readings.

13. The method of claim 11, further comprising:
- calculating a time interval based on the angular-dependence objective and the speed of the object conveyor, wherein activating the one or more second illumination-detection devices is performed when the time interval has elapsed since activating the one or more first illumination-detection devices.

14. The method of claim 10, further comprising:
- selecting the one or more first illumination-emission devices and the one or more first illumination-detection devices based on the first light-measurement objective; and
- selecting the one or more second illumination-emission devices and the one or more second illumination-detection devices based on the second light-measurement objective.

15. The method of claim 10, wherein a setting value for an illumination-emission device defines a value for one of the following: spectral band, intensity, illuminance, and polarization.

16. The method of claim 10, wherein a setting value for an illumination-detection device defines a value for one of the following: exposure, spectral band, gain, and dynamic range.

17. A device for inspecting materials, the device comprising:
- a computer memory; and
- one or more processing units that are coupled to the computer memory, to an object conveyor that has an adjustable speed, to one or more illumination-emission devices, and to one or more illumination-detection devices, wherein the one or more processing units are configured to cause the device to
  - obtain an angular-dependence objective, wherein the angular-dependence objective defines a difference between a first light-reflection angle and a second light-reflection angle;
  - select a speed of the object conveyor based on the angular-dependence objective;
  - initiate motion of the object conveyor at the speed;
  - configure one or more first illumination-emission devices and one or more first illumination-detection devices according to first settings values;
  - activate the one or more first illumination-emission devices;
  - activate the one or more first illumination-detection devices to generate first illumination readings;
  - configure one or more second illumination-emission devices and one or more second illumination-detection devices according to second settings values;
  - activate the one or more second illumination-emission devices; and
  - activate the one or more second illumination-detection devices to generate second illumination readings.

18. The device of claim 17, wherein the one or more processing units are further configured to cause the device to select the speed based on respective positions of the one or more first illumination-emission devices, on respective positions of the one or more second illumination-emission devices, on respective positions of the one or more first illumination-detection devices, and on respective positions of the one or more second illumination-detection devices.

19. The device of claim 17, wherein the one or more processing units are further configured to cause the device to
calculate a time interval based on the speed of the object conveyor; and
activate the one or more second illumination-detection devices when the time interval has elapsed since activating the one or more first illumination-emission devices.

20. The device of claim 19, wherein the one or more processing units are further configured to cause the device to
configure one or more third illumination-emission devices and one or more third illumination-detection devices according to third settings values;
activate the one or more third illumination-emission devices; and
activate the one or more third illumination-detection devices to generate third illumination readings.

* * * * *